(12) United States Patent
Hartman

(10) Patent No.: US 6,964,067 B1
(45) Date of Patent: Nov. 15, 2005

(54) HINGED GOGGLE

(75) Inventor: James Hartman, Santa Monica, CA (US)

(73) Assignee: Utopia Optics International, Inc.

( * ) Notice: Subject to any disclaimer, the term of this patent is extended or adjusted under 35 U.S.C. 154(b) by 26 days.

(21) Appl. No.: 10/830,519

(22) Filed: Apr. 22, 2004

(51) Int. Cl.[7] ............................................. A61F 9/02
(52) U.S. Cl. ...................................................... 2/431
(58) Field of Search ........................... 2/443, 429, 434, 2/441, 453, 431, 436

(56) References Cited

U.S. PATENT DOCUMENTS

| | | | |
|---|---|---|---|
| 2,718,007 A | 9/1955 | Schauweker | |
| 3,016,543 A | 1/1962 | Lindblom | |
| 3,276,034 A | 10/1966 | Cupp | |
| 3,782,810 A | 1/1974 | Marker | ........................ 351/47 |
| 4,724,546 A | 2/1988 | Cumbie, Jr. | ...................... 2/12 |
| 4,901,374 A | 2/1990 | VanderWoude | ................... 2/10 |
| 5,347,655 A | 9/1994 | Garrett | ............................ 2/10 |
| D377,036 S | 12/1996 | Leonardi | ................... D16/304 |
| 5,652,954 A | 8/1997 | Paiement et al. | ................. 2/10 |
| 5,752,280 A | 5/1998 | Hill | ............................... 2/453 |
| D408,431 S | 4/1999 | Simioni | ..................... D16/312 |
| 6,178,561 B1 | 1/2001 | Cheng | ............................ 2/431 |
| 6,282,727 B1 * | 9/2001 | Lindahl | ......................... 2/428 |
| 6,357,053 B1 | 3/2002 | Wang Lee | ...................... 2/431 |
| D457,909 S | 5/2002 | Wang-Lee | ..................... D16/6 |
| D477,010 S | 7/2003 | Moritz et al. | .............. D16/312 |

\* cited by examiner

*Primary Examiner*—John Calvert
*Assistant Examiner*—Brian Kauffman
(74) *Attorney, Agent, or Firm*—Cislo & Thomas LLP

(57) ABSTRACT

An eye protection device is disclosed herein. The eye protection device includes a face frame, a lens frame, and a means for pivotally coupling the lens frame to the face frame, wherein the lens frame is selectively positionable with respect to the face frame.

26 Claims, 3 Drawing Sheets

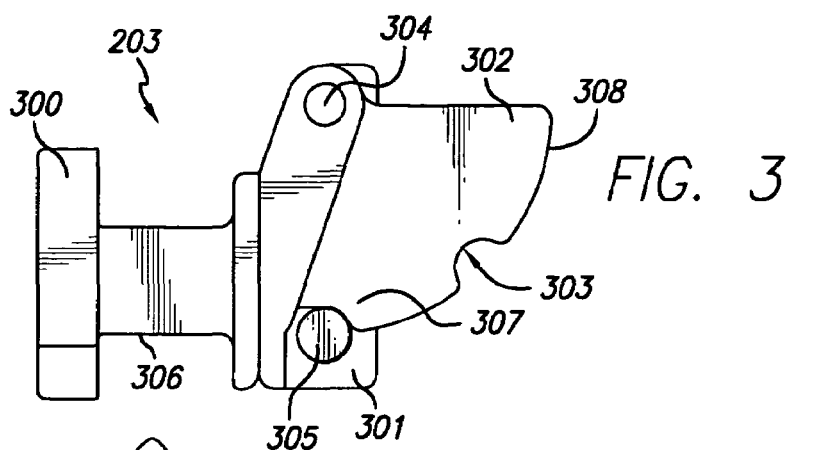
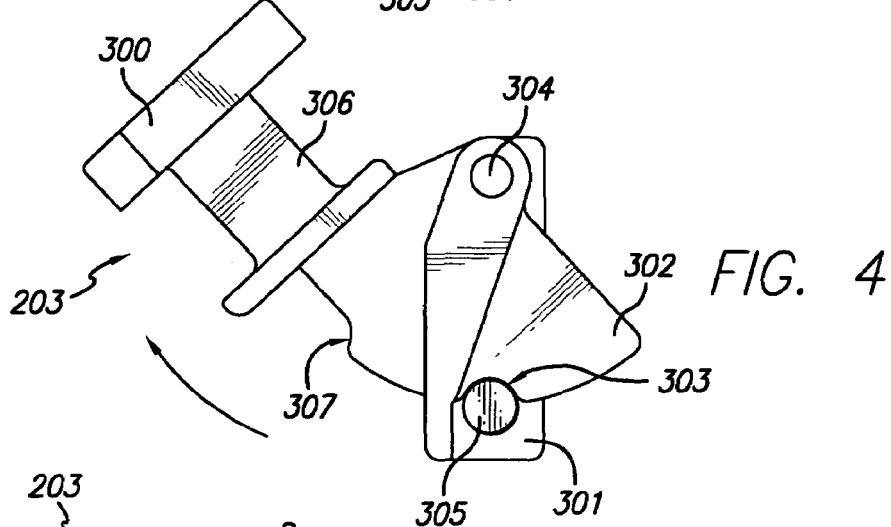
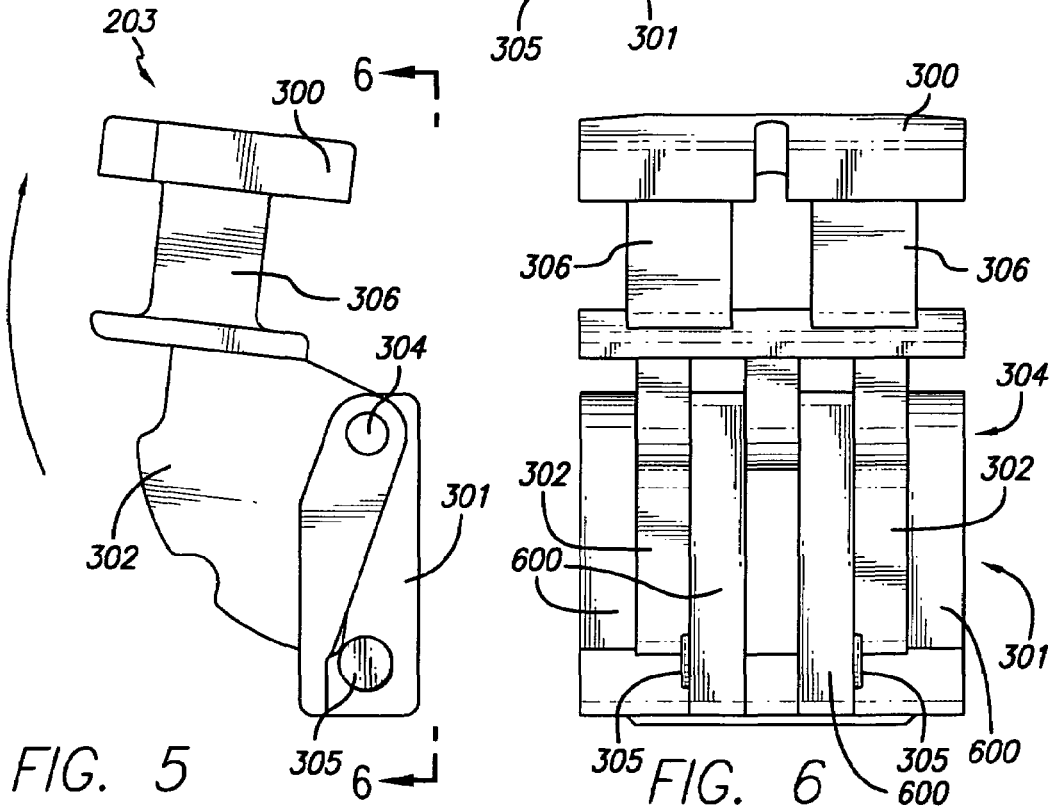

HINGED GOGGLE

BACKGROUND

Various types of eye protection devices have developed in the prior art such as goggles, eyeglasses, visors, shields, or the like. These goggles may be used in a variety of applications such as, but not limited to, manufacturing or recreational purposes. With respect to recreational uses, various goggles have been developed for skiing, snowboarding, or other activities where the user intends to protect one's eyes. In the prior art, goggles have been developed where a portion of the goggle may be flipped up so that the lens portion of the goggle is removed from the user's line of sight. While these prior art goggles having a moveable lens are useful, there still remains a need for an eye protection device such as a goggle wherein a portion of the goggle remains fixed to the user's face when the lens is flipped up or otherwise moved out of the user's line of sight.

SUMMARY

Exemplary embodiments disclosed herein are directed to eye protection devices having a lens frame and an associated lens that is pivotally coupled to the face frame such that the frame and associated lens may be "flipped up" or otherwise moved out of the user's line of sight while the face frame remains fixed to the user's face. According to one exemplary embodiment, the eye protection device is composed of a lens frame and associated lens, a face frame, and a means for pivotally coupling the lens frame to the face frame, wherein the lens frame is selectively positionable with respect to the face frame.

In another exemplary embodiment, the eye protection device includes a lens coupled to a lens frame, wherein the lens frame is pivotally coupled to a face frame by a hinge. The hinge allows the lens frame to be selectively positionable with respect to the face frame. The eye protection device also includes an adjustable strap having a first end and a second end, wherein the first end of the adjustable strap is coupled to a portion of the face frame and the second end of the adjustable strap is coupled to an opposite portion of the face frame.

BRIEF DESCRIPTION OF THE DRAWINGS

FIG. 1A is an enlarged cross sectional view of the eye protection device of FIG. 1 taken along line 1A—1A;

FIG. 3 is an enlarged side view of an exemplary embodiment of a hinge used in the eye protection device of FIG. 1;

FIG. 4 is an enlarged side view of the exemplary hinge embodiment of FIG. 3 wherein the hinge is in a partially opened position;

FIG. 5 is an enlarged side view of the exemplary hinge embodiment of FIG. 3 wherein the hinge is in a fully opened position; and FIG. 6 is an enlarged rear view of the exemplary hinge embodiment in a fully opened position.

DETAILED DESCRIPTION

The detailed description set forth below in connection with the appended drawings is intended as a description of exemplary embodiments and is not intended to represent the only forms in which the exemplary embodiments may be constructed and/or utilized. The description sets forth the functions and the sequence of steps for operating the exemplary embodiments. However, it is to be understood that the same or equivalent functions and sequences may be accomplished by different embodiments that are also intended to be encompassed within the spirit and scope of the specification.

Figure 1:
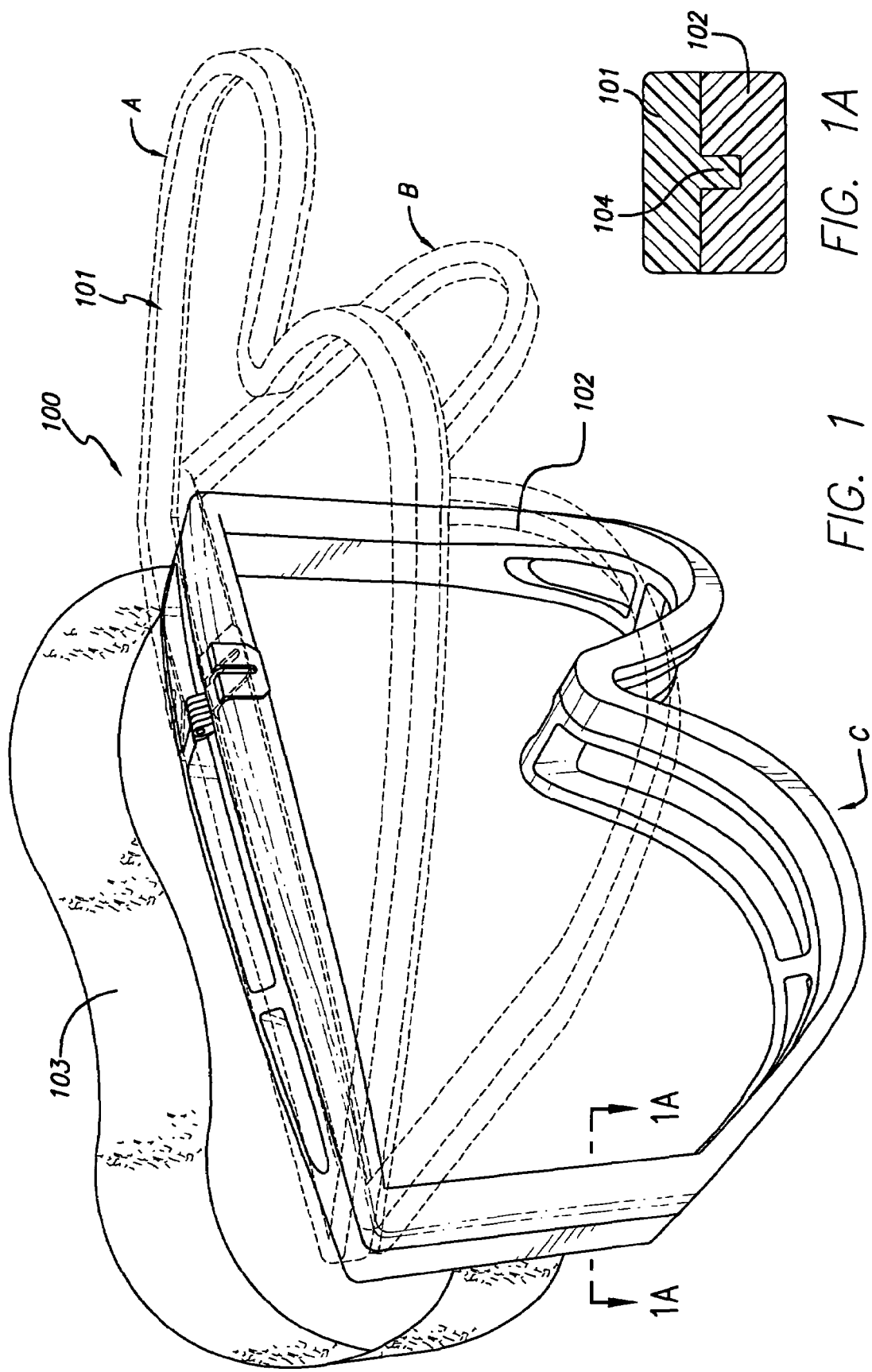
FIG. 1 is a perspective view of an exemplary embodiment of an eye protection device wherein the lens frame is selectively positionable with respect to the face frame.

Turning now to the figures, FIG. 1 illustrates one exemplary embodiment of the eye protection device 100. As shown in FIG. 1, the eye protection device 100 includes a face frame 102 and a lens frame 101. An adjustable strap 103 is coupled to opposite sides of the face frame in order to secure the eye protection device 100 to the face of the user. The lens frame 101 may be selectively positional with respect to the face frame 102 at positions A, B, and C. In position A, the lens frame 101 is in an open or upright position such that the lens frame is positioned approximately 90° with respect to the face frame 102. In position B, the lens frame 101 is in spaced relationship to the face frame 102. In one embodiment, the lens frame 101 is at an angle approximately 45° from the face frame. In position C, the lens frame 101 is positioned such that the lens frame 101 contacts the face frame 102. In other embodiments, the lens frame 101 may be selectively positionable at one or more positions between approximately 1° to approximately 180° with respect to the face frame 102.

When the lens frame 101 is in positions A or B, the user is able to provide additional ventilation to the lens and user's face without removing the eye protection device 100 from the user's face. In another exemplary embodiment, the ability to flip-up the lens frame 101 from the face frame 102 allows the user to remove any polarized or dark lens that may be associated with the lens frame from the user's line of sight. Also, the user may clean the inner surface of the lens without removing the eye protection device 100 from one's face.

Figure 2:
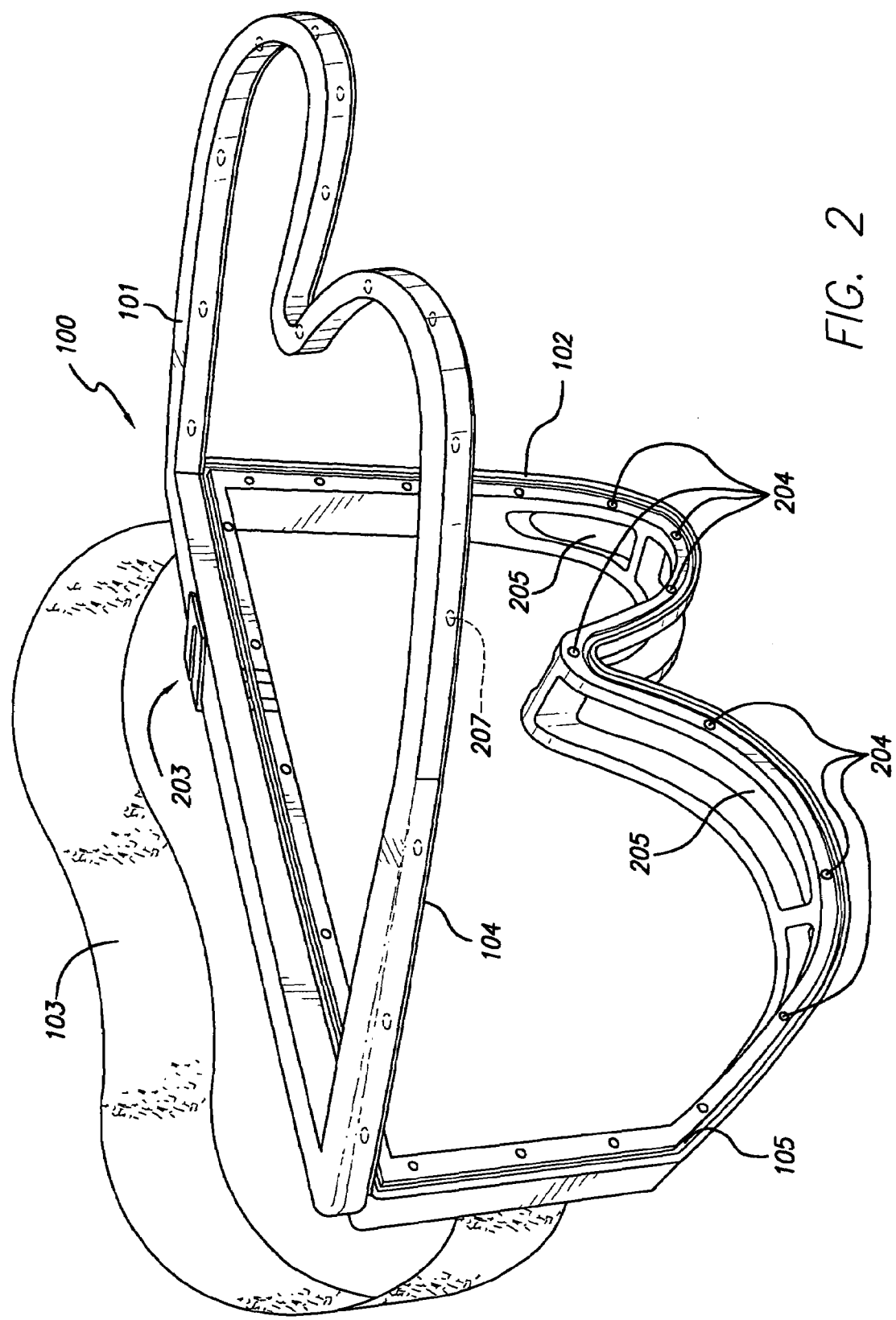
FIG. 2 is a perspective view of an exemplary embodiment of FIG. 1 wherein the lens frame is in an open position.

The eye protection device 100 can include a means for sealing the space between the face frame 102 and the lens frame 101 when in position C. The means may be a "tongue" 104 and "groove" 105 interlocking connection as shown in FIG. 2. In other embodiments, the means may be other sealing means known or developed in the art. As those skilled in the art will appreciate, the "tongue" 104 and "groove" 105 interlocking connection may be made of rigid, elastomeric, foam, or any other material suitable for creating an interlocking relationship between two surfaces.

As shown in FIG. 1A, the lens frame 101 and the face frame 102 have corresponding tongue 104 and groove 105 interlocking connection. In one embodiment, the tongue portion 104 or extending ridge is provided on the lens frame 101 and a corresponding groove 105 is provided on the face frame 102. In an alternate embodiment, the tongue portion 104 is provided on the face frame 102 and the groove 105 portion is provided on the lens frame 101. The tongue 104 and groove 105 interlocking connection provided on the periphery of the face frame 102 and lens frame 101 prevent moisture, snow, dirt, and other debris from entering the interior of the eye protection device 100.

FIG. 2 illustrates the eye protection device 100 wherein the lens frame 101 is substantially perpendicular to the face frame 102. As shown in FIG. 2, the face frame 102 includes a generally horizontally-extending brow portion that is coupled to or integral with a generally arcuate shaped bottom that is sized to fit over the user's cheek and nose. Additionally, the face frame 102 includes a plurality of vents 205 that may be positioned about the perimeter of the face frame 102. As shown in FIG. 2, the ventilation ports 205 are positioned on the lower portion of the face frame 102. In an alternate embodiment, the ventilation ports 205 may be positioned at the top of the face frame 102. In yet another embodiment, the ventilation ports 205 may be positioned at both the top and bottom of the face frame 102.

In another embodiment, the ventilation ports 205 may be positioned on the sides of the face frame 102. In yet another embodiment, the ventilation ports on the sides of the face frame 103 may be combined with ventilation ports 205 that are positioned on the top, bottom, or combinations thereof. The ventilation ports 205 are designed to allow moving air to enter the interior of the goggle while directing the air flow towards the interior sides of the lens to prevent lens fogging.

As shown in FIG. 2, the face frame 102 includes a plurality of magnets 204 that are positioned about the periphery of the face frame 102. Additionally, the lens frame 101 includes corresponding magnets 207 that engage the magnets 204 on the face frame. In another embodiment, the face frame material 102 may be magnetized to attract the lens frame material 101 wherein the lens frame includes metal inserts. In another embodiment, the lens frame 101 includes corresponding metal inserts to attract corresponding magnets. In yet another embodiment, face frame material 102 may be magnetized to attract the lens frame material 101. Accordingly, the magnets 204, 207 secure the lens frame 101 to the face frame 102 in a closed position C. That is, the magnets 204, 207 prevent the lens frame 101 from being accidentally dislodged or separated from the face frame 102 of the eye protection device 100. As shown in FIG. 2, the magnets 204, 207 have a generally circular shape, but those skilled in the art will appreciate that the magnets 204, 207 may have a plurality of shapes and sizes. In other embodiments, the magnets 204, 207 may be placed at different locations about the periphery of the face frame 101 and lens frame 102 other than those locations depicted in FIG. 2. As those skilled in the art will appreciate, the lens frame 101 may be reversibly securable to the face frame 102 by providing various means of attraction such as, but not limited to, magnet to magnet, magnet to metal, magnetic impregnated plastic, and all other types of magnetic attraction known or developed in the art.

As shown in FIG. 2, the eye protection device 100 also includes a hinge 203. As shown in the embodiment depicted in FIG. 2, the hinge 203 may be affixed to or encapsulated to the top portion of the face frame 102 and a corresponding portion on the lens frame 101. In one exemplary embodiment, the hinge 203 may be positioned on the center of the face frame 102. In another embodiment, the hinge 203 may be offset to one side of the face frame 102. In yet another embodiment, the eye protection device 100 may have one or more hinges 203 positioned on the face frame 102. For instance, in one embodiment, the hinges 203 may be located at the ends of the face frame 102. In another embodiment, the hinges 203 may be centrally positioned on the top portion of the face frame 102. In yet another embodiment, the hinge may be a living hinge consisting of material from both frames 101 and 102 of the eye protection device 100. The hinge may be a living, encapsulated, inserted, affixed, or secured hinge known or developed in the art.

Turning to FIG. 3, the hinge 203 is composed of a first bracket 300 and a second bracket 301. The first bracket 300 is coupled to the lens frame 101 of the eye protection device 100. The second bracket 301 is fixed to the face frame 102 of the eye protection device 100. FIG. 3 illustrates the hinge 203 when the lens frame 101 is in a closed position with respect to the face frame 102 as shown in position C of FIG. 1.

The first bracket 300 includes a lens frame coupling portion 306 and articulating wedge-shaped member 302. As shown in FIG. 3, the lens frame coupling portion 306 and the wedge-shaped member 302 is an integral structure. In another embodiment, the coupling portion 306 and the wedge-shaped member 302 may be separate components that are also fixed together. The wedge-shaped members 302 are generally planar structures having a curved bottom surface 308. The wedge-shaped member 302 includes a plurality of one or more recesses 303, 307 spaced along the curved surface 308 which are sized to engage an interlocking member 305.

As shown in FIG. 6, the first bracket 300 may include any number of coupling structures including two lens frame coupling structures 306 and a plurality of wedge-shaped members 302. In another embodiment, the first bracket 300 may have one frame coupling structure 306 fixed to a plurality of wedge-shaped members 302. In another embodiment, the first bracket 300 may include two wedge-shaped members 302 as shown in FIG. 6. In other embodiments, the first bracket 300 may include one or more wedge-shaped members 302.

As shown in FIG. 6, the second bracket 301 is composed of at least two fingers 600. The fingers 600 are spaced apart and interwoven with the wedge-shaped members 302 of the first bracket 300. The second bracket 301 also includes an interlocking member 305 that extends from the outer surface of at least two fingers 600. As shown in FIG. 6, the fingers 600 of the second bracket 301 are generally spaced apart and are sized to engage the wedge-shaped member 302 of the first bracket 300. These interlocking members 305 engage the recesses 303, 307 that are provided on the wedge-shaped member 302. When the interlocking member 305 is engaged in the recesses 303, 307 the lens frame 101 is then locked into a position relative to the face frame 102. As shown in FIG. 3, the first bracket 300 and a second bracket 301 are pivotally coupled together at a pivot point 304.

FIG. 4 illustrates the hinge 203 when the lens frame 101 is in position B as depicted in FIG. 1. The hinge 203 is now locked as the interlocking member 305 has engaged the recess 303 that is positioned on the curved face 308 on the wedge-shaped member portion 302 of the first bracket 300. The first bracket 300 is pivotable about the pivot point 304 until the recess of 303 and 307 accept the protruding member of 305.

FIG. 5 illustrates the hinge 203 in the fully opened position (position A of FIG. 1). The end of the curved portion 308 has been pivoted beyond the interlocking member 305, and the corner of the wedge-shaped member 302 rests upon the interlocking member 305. As those skilled in the art will appreciate, the hinge 203 may have a plurality of recesses 303 such that the lens frame 101 may be open to various points along the curved portion 308 of the wedge-shaped member 302. The hinge 203 allows the user to move the lens frame 101 with respect to the face frame 102 and lock the lens frame 101 at various positions from the face frame 102.

As shown in FIG. 6, the hinge 203 includes a first bracket 300 and a second bracket 301. The various members 302, 600 of the first bracket 300 and the second bracket 301, respectively, are interwoven and interconnected at a pivot point 304. The respective members 302, 600 of the first and second bracket are adjacent to one another and may or may not have a very small clearance. The small clearance allows the interlocking member 305 to be a relatively small protuberance that extends from the fingers 600 of the second bracket 301.

In yet another embodiment, the hinge 203 may be encapsulated or fixed onto each frame. In yet another embodiment, the hinge 203 may be configured such that the lens and the lens frame 101 may be removable or detached from the face frame 102. Furthermore, as those skilled in the art will appreciate, the hinge 203 does not need to index.

In use, the eye protection device 100 may be used for a myriad of activities where individual needs to protect their eyes from the elements, debris, or objects. For instance, the eye protection device 100 may be used in winter activates such as, but not limited to, skiing, snow-boarding, snow mobiling, snow shoeing, cross country skiing, or the like. Alternatively, the goggles may be used for motor sports such as, but not limited to, motor-cross, racecar driving, or the like. As those skilled in the art will appreciate, the eye protection devices 100 disclosed herein may be utilized in those activates where an individual user desires ones eyes.

In closing, it is to be understood that the embodiments described herein are illustrative of the principles of the exemplary embodiment. Thus, by way of example, but not of limitation, alternative configurations or modifications may be utilized in accordance with the teachings herein. Accordingly, the drawings and description are illustrative and not meant to be a limitation thereof.

What is claimed is:

1. An eye protection device, comprising:
   an face frame, the face frame peripherally defining an opening to extend across a wearer's line of sight when secured to the wearer's face;
   a lens frame pivotally coupled to the face frame for pivotal displacement relative thereto, wherein the lens frame is selectively positionable with respect to the face frame;
   the lens frame being thereby displaceable to provide ventilation to the wearer's face without removal of the face frame from contact below the wearer's eyes.

2. The eye protection device of claim 1 further comprising a means for securing the lens frame to the face frame.

3. The eye protection device of claim 2 wherein the securing means comprises one or more magnetic elements positioned about a periphery of the face frame and corresponding magnetic elements positioned about a periphery of the lens frame.

4. The eye protection device of claim 1 wherein the face frame further comprises a brow portion coupled to a frame portion configured to fit over a cheek and a nose of an individual.

5. The eye protection device of claim 1 wherein the face frame further comprises an adjustable strap having a first end and a second end, wherein the first end of the adjustable strap is coupled to a portion of the face frame and the second end of the adjustable strap is coupled to an opposite portion of the face frame.

6. The eye protection device of claim 1 further comprising a means for sealing the lens frame to the face frame.

7. The eye protection device of claim 1 wherein the coupling means is a hinge positioned on a central portion of the face frame and the lens frame.

8. The eye protection device of claim 7 wherein the lens frame contacts the face frame when the hinge is in a first position.

9. The eye protection device of claim 8 wherein the lens frame is at an angle approximately 45° from the face frame when the hinge is in a second position to allow increased open air ventilation.

10. The eye protection device of claim 9 wherein the lens frame is substantially perpendicular to the face frame when the hinge is in a third position.

11. An eye protection device, comprising:
    a face frame peripherally defining an opening to extend across a wearer's line of sight when secured to the wearer's face;
    a lens coupled to a lens frame;
    the lens frame pivotally coupled to the face frame by a hinge for pivotal displacement relative thereto, the lens frame being thereby displaceable to provide ventilation to the wearer's face without removal of the face frame from contact below the wearer's eyes
    the hinge comprising a first bracket pivotally coupled to a second bracket, wherein the first bracket is coupled to the face frame and a second bracket is coupled to the lens frame by a close tolerance rod, a threaded hardware, or a penetrating member used to bind the first bracket to the second bracket,
    the first bracket comprises at least two fingers and at least one interlocking member positioned on an outer surface of the at least two fingers, and
    the second bracket comprises at least two wedge-shaped members coupled to a lens frame coupling portion, the at least two wedge-shaped members having curved bottom surface having one or more recesses sized to engage the interlocking member on the fingers of the first bracket; and
    an adjustable strap having a first end and a second end, wherein the first end of the adjustable strap is coupled to a portion of the face frame and the second end of the adjustable strap is coupled to an opposite portion of the face frame.

12. The eye protection device of claim 11 wherein the face frame further comprises a brow portion coupled to a frame portion configured to fit over a cheek and a nose of an individual.

13. The eye protection device of claim 11 further comprising a means for securing the lens frame to the face frame.

14. The eye protection device of claim 13 wherein the securing means comprises one or more magnets positioned about a periphery of the face frame and corresponding magnetic elements positioned about periphery of the lens frame.

15. The eye protection device of claim 11 further comprising a means for sealing the lens frame to the face frame.

16. The eye protection device of claim 11 wherein the first bracket comprises one or more interlocking fingers in spaced relation, wherein the interlocking members are positioned on the outer surface of the centrally positioned fingers.

17. The eye protection device of claim 16 wherein the second bracket comprises one or more wedge-shaped members.

18. An eye protection device, comprising:
    a face frame pivotally coupled to a lens frame,
    the face frame peripherally defining an opening to extend across a wearer's line of sight when secured to the wearer's face; the face frame sized and shaped to engage the face of an individual, the face frame having one or more ventilation ports positioned on a lower portion of the face frame;
    the lens frame sized and shaped to engage the face frame, and the lens frame coupled to a lens;

the lens frame pivotally coupled to the face frame by a hinge for pivotal displacement relative thereto, the lens frame being thereby displaceable to provide ventilation to the wearer's face without removal of the face frame from contact below the wearer's eyes the hinge comprising a first bracket pivotally coupled to a second bracket, wherein the first bracket is coupled to the face frame and a second bracket is coupled to the lens frame, the first bracket comprises at least two fingers and at least one interlocking member positioned on an outer surface of the at least two fingers, and the second bracket comprises at least two wedge-shaped members coupled to a lens frame coupling portion, the at least two wedge-shaped members having curved bottom surface having one or more recesses sized to engage the interlocking member on the fingers of the first bracket;

one or more magnets positioned about a periphery of the face frame and corresponding magnets positioned about a periphery of the lens frame; and an adjustable strap having a first end and a second end, wherein the first end of the adjustable strap is coupled to a portion of the face frame and the second end of the adjustable strap is coupled to an opposite portion of the face frame.

19. The eye protection device of claim 18 wherein the hinge is a living hinge, an encapsulated hinge, an inserted hinge, an affixed hinge, or a secured hinge.

20. The eye protection device of claim 18 wherein the hinge is positioned on a central portion of the face frame.

21. The eye protection device of claim 20 wherein the first bracket comprises four fingers in spaced relation, wherein the interlocking members are positioned on the outer surface of the centrally positioned fingers.

22. The eye protection device of claim 21 wherein the second bracket comprises two wedge-shaped members.

23. The eye protection device of claim 22 wherein the lens frame contacts the face frame when the hinge is in a first position.

24. The eye protection device of claim 23 wherein the lens frame is at an angle approximately 45° from the face frame when the hinge is in a second position.

25. The eye protection device of claim 24 wherein the lens frame is substantially perpendicular to the face frame when the hinge is in a third position.

26. The eye protection device of claim 21 further comprising a means for sealing the lens frame to the face frame.

* * * * *